(12) United States Patent
Swords et al.

(10) Patent No.: US 9,433,707 B2
(45) Date of Patent: *Sep. 6, 2016

(54) BONE GRAFT MATERIAL CONTAINMENT STRUCTURES

(75) Inventors: Greg Alan Swords, Atlanta, GA (US); Daniel Bruce Spagnoli, Denver, NC (US)

(73) Assignee: Orthovita, Inc., Malvern, PA (US)

( * ) Notice: Subject to any disclaimer, the term of this patent is extended or adjusted under 35 U.S.C. 154(b) by 1027 days.

This patent is subject to a terminal disclaimer.

(21) Appl. No.: 12/712,949

(22) Filed: Feb. 25, 2010

(65) Prior Publication Data

US 2010/0215718 A1 Aug. 26, 2010

Related U.S. Application Data

(60) Provisional application No. 61/208,539, filed on Feb. 25, 2009.

(51) Int. Cl.
| | |
|---|---|
| A61F 2/00 | (2006.01) |
| A61L 27/56 | (2006.01) |
| A61F 2/28 | (2006.01) |
| A61L 27/12 | (2006.01) |
| A61L 27/16 | (2006.01) |
| A61L 27/22 | (2006.01) |
| A61L 27/36 | (2006.01) |
| A61L 27/38 | (2006.01) |
| A61L 27/54 | (2006.01) |

(Continued)

(52) U.S. Cl.
CPC .............. *A61L 27/56* (2013.01); *A61F 2/2803* (2013.01); *A61F 2/2846* (2013.01); *A61L 27/12* (2013.01); *A61L 27/16* (2013.01); *A61L 27/227* (2013.01); *A61L 27/365* (2013.01); *A61L 27/3608* (2013.01); *A61L 27/38* (2013.01); *A61L 27/54* (2013.01); *A61F 2/30724* (2013.01); *A61F 2/4455* (2013.01); *A61F 2002/2817* (2013.01); *A61F 2002/2835* (2013.01); *A61F 2002/3092* (2013.01); *A61F 2002/30576* (2013.01); *A61F 2002/30915* (2013.01); *A61F 2310/00011* (2013.01); *A61L 2300/414* (2013.01); *A61L 2300/64* (2013.01); *A61L 2430/02* (2013.01)

(58) Field of Classification Search
None
See application file for complete search history.

(56) References Cited

U.S. PATENT DOCUMENTS

| | | |
|---|---|---|
| 3,849,805 A | 11/1974 | Leake et al. |
| 4,455,256 A | 6/1984 | Urist |
| 4,472,840 A | 9/1984 | Jefferies |

(Continued)

FOREIGN PATENT DOCUMENTS

CN 101134118 A 3/2008

OTHER PUBLICATIONS

Porex, 2007-2008 Cranial/Neurosurgical Update (2007).*

(Continued)

*Primary Examiner* — Thomas J Visone
(74) *Attorney, Agent, or Firm* — Lerner, David, Littenberg, Krumholz & Mentlik, LLP

(57) ABSTRACT

The present invention provides biocompatible, non-resorbable porous containment structures for containment of bone graft material at a desired location for stimulation of bone growth. The porous containment structures have interconnected pores sized to allow fibrovascular integration with surrounding tissue and conduction of vascular tissue through the structure into the bone graft material.

21 Claims, 8 Drawing Sheets

(51) Int. Cl.
*A61F 2/30* (2006.01)
*A61F 2/44* (2006.01)

(56) References Cited

U.S. PATENT DOCUMENTS

| | | | |
|---|---|---|---|
| 4,636,215 A | | 1/1987 | Schwartz |
| 4,693,721 A | * | 9/1987 | Ducheyne .................. 623/23.54 |
| 4,976,737 A | | 12/1990 | Leake |
| 5,380,329 A | | 1/1995 | Elia et al. |
| 5,989,289 A | * | 11/1999 | Coates et al. .............. 623/17.16 |
| 6,031,148 A | | 2/2000 | Hayes et al. |
| 6,113,640 A | * | 9/2000 | Tormala et al. ........... 623/18.11 |
| 6,132,214 A | * | 10/2000 | Suhonen et al. ........... 433/201.1 |
| 6,136,029 A | * | 10/2000 | Johnson et al. ........... 623/16.11 |
| 6,139,574 A | * | 10/2000 | Vacanti et al. ............... 623/1.44 |
| 6,409,764 B1 | | 6/2002 | White et al. |
| 6,530,955 B2 | * | 3/2003 | Boyle et al. ............... 623/17.11 |
| 6,989,029 B2 | * | 1/2006 | Bonutti ...................... 623/11.11 |
| 7,066,962 B2 | * | 6/2006 | Swords ...................... 623/17.18 |
| 7,192,450 B2 | | 3/2007 | Brauker et al. |
| 2001/0020188 A1 | * | 9/2001 | Sander ....................... 623/23.57 |
| 2001/0049560 A1 | * | 12/2001 | Paul et al. .................. 623/17.16 |
| 2004/0167625 A1 | * | 8/2004 | Beyar et al. ............... 623/11.11 |
| 2005/0043733 A1 | * | 2/2005 | Eisermann et al. ............. 606/61 |
| 2005/0214340 A1 | * | 9/2005 | Erbe et al. .................... 424/423 |
| 2005/0281856 A1 | * | 12/2005 | McGlohorn et al. ......... 424/423 |
| 2005/0288790 A1 | * | 12/2005 | Swords ...................... 623/17.19 |
| 2006/0224242 A1 | | 10/2006 | Swords et al. |
| 2007/0129804 A1 | * | 6/2007 | Bentley et al. ............ 623/17.11 |
| 2008/0167686 A1 | * | 7/2008 | Trieu et al. ................... 606/249 |

OTHER PUBLICATIONS

Rah, Yonsei Med. J., vol. 41, No. 6, pp. 756-765 (2000).*
Karnes et al, Aesthetic Surg. J., vol. 20, No. 1 pp. 26-30 (2000).*
Medpor, Biomaterial 2007-2008 Oculoplastics update, pp. 1-12 (2007).*
Synthes, chronOS Bone Void Filler, technical brochure (2008).*
Synthes, Spine Biomaterial Solutions (2008).*
Lie et al., Neurosurg. Focus, 16(3):Clinical Pearl 1 (2004).*
International Search Report and Written Opinion, PCT/US2010/025431, Dated Mar. 30, 2011.
Naik Milind N. et al. : "Comparison of Ascularization of Medpor and Medpor-Plus Orbital Implants: A Prospective, Randomized Study." Ophthalmic Plastic and Reconstructive Surgery, vol. 23, No. 6, Nov. 1, 2007, pp. 463-467, XP002627046.
Boyne et al., J Oral Maxillofac Surg., 63(12), 1693-707, Dec. 2005—Abstract.
Florellini et al., J. Periodontol, 76(4), 605-613, Apr. 2005—Abstract.
Osseonews.com—Dental Implant Information and Discussion, www.osseonews.com, date unknown.
Triplett et al., J Oral Maxillofac Surg., 67(9), 1947-1960, Sep. 2009—Abstract.
W.L. Gore & Associates, Gore-Tex Regenerative Membrane, Instructional broshure, Feb. 2003.

* cited by examiner

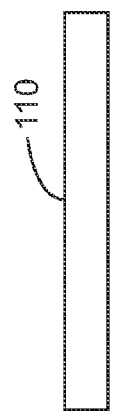
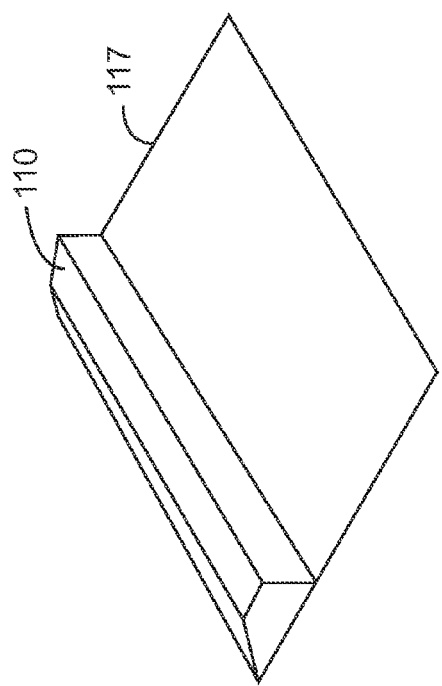
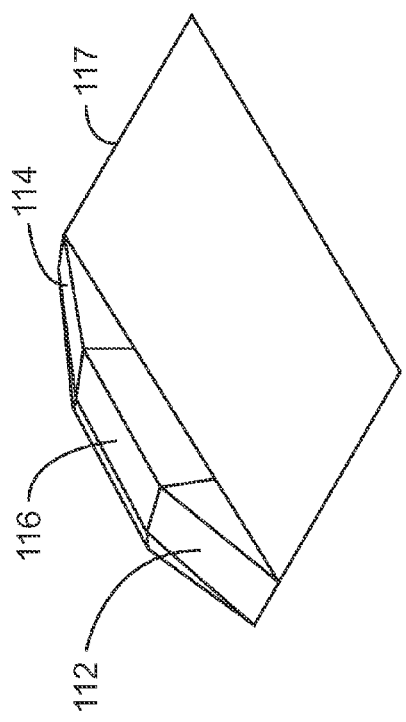

BONE GRAFT MATERIAL CONTAINMENT STRUCTURES

PRIOR RELATED APPLICATIONS

The present application claims the benefit of priority to U.S. Provisional Application No. 61/208,539 filed Feb. 25, 2009, which is incorporated herein by reference in its entirety.

FIELD OF THE INVENTION

Embodiments of the present invention relate generally to containment structures used in connection with bone graft materials, as well as devices, methods, and systems for containing bone graft material in place during reconstructive surgery. Certain embodiments provide a tissue-integrating or porous polymer material that can be formed by a surgeon, provided as sheets, provided as pre-shaped structures, or that can be provided in semi-custom or custom forms, in order to maintain the tissue space shape and form required for a bone graft of the craniofacial or appendicular skeleton. Other embodiments relate to surgical methods that are used to encourage bone growth using a bone graft material and porous polymer material. Specific embodiments are particularly useful for various oral surgery and/or dental applications.

BACKGROUND

Surgical reconstruction of bone defects is becoming increasingly common. Reconstruction may be needed due to tooth loss, infections, trauma, congenital defects, tumors, malignant diseases such as cancer, periodontal disease, or for a multitude of other reasons. In specific instances, the bone defect may be located in a patient's oral cavity or in the maxillary, mandibular, or palatine bones.

Some surgical techniques seek to encourage bone growth ("osteogenesis") as well as reconstruct the bone. For example, encouraging new bone growth may help provide a fixation point for a permanent implant (e.g., in order to fix a dental implant in place), or it may be necessary when the defect is too large to repair with fixation. This is especially true in the context of oral, facial, and maxillofacial surgery. Applied to reconstruction of the mandible or maxilla, bone grafting can allow osteogenesis to occur across a gap that would not otherwise be bridged by new bone.

Bone graft materials have been used to attempt to establish new bone in a bony defect area of the body. Non-limiting examples of such bone graft materials include autologous bone, autologous bone particulate, allogenic bone graft material, human cadaver bone, xenograft bone graft material, animal bone, or synthetic materials such as hydroxyapatite, tricalcium phosphate, bioactive glass, growth factors and others. Often the patient's blood or autologous bone particles are mixed with cadaver, animal, or synthetic materials to accelerate the healing process. This technique is designed to encourage the body's normal bone healing process to extend from existing viable bone through the material and result in new bone in the area of the graft material. However, adjacent fibrous or soft tissue will often attempt to heal or migrate into the area of the graft material. In some situations, and especially in larger graft areas having direct contact with fibrous or soft tissue, the resulting healed tissue will be fibrous tissue rather than bone tissue, because fibrous tissue invades and heals more quickly than bone.

To address these problems, some surgeons have placed a complete barrier material over the bone graft material before covering it with the overlying fibrous or soft tissue in order to prevent the ingrowth of fibrous tissue. Such barriers are intended to exclude cells and newly growing blood vessels, allowing the bone graft material to heal from the areas where it contacts bone, thus encouraging only bone healing and excluding fibrous or soft tissue healing from the site. For example, one material that has been used for this purpose is expanded polytetrafluroethylene (ePTFE) which serves as a cell barrier, having a pore size in the range of about 20 microns in diameter. This membrane typically must be removed after a few months in an additional surgical procedure.

A specific commercially available material that provides a cell barrier for periodontal tissue regeneration is the GORE-TEX® Regenerative Membrane (W.L. Gore and Associates, Newark, Del.). This periodontal material is made of ePTFE and is used to provide a cell barrier between the gingiva and a periodontal defect. It is intended to preserve the necessary space between the surface of the defect and the desired contours of the subsequently regenerated surface.

It is believed that GORE-TEX®'s pore size is about 20 microns, which may allow blood infiltration and some invasion of fibrous connective tissue, but this pore size is not large enough to allow vascular infiltration (e.g., fibrovascular tissue growth into and through the material). Blood vessels are not able to penetrate the GORE-TEX® material and thus, do not provide a vascular supply to the bone graft material. Such barrier materials are desired for certain bone grafts in order to exclude fibrovascular tissue from the bone healing site, and to allow bone to heal from the edges of the bony defect into the bone graft material.

More recently, resorbable membrane materials have also been used, which do not always have to be removed. One commercially available example is VICRYL® Periodontal Mesh from Johnson & Johnson, made of woven fibers of a bioabsorbable copolymer (about 90% glycolide and 10% lactide). VICRYL® mesh is similar to a fabric. One of its drawbacks is that it does not have the stiffness to maintain a specific shape. It can also cause undesirable hydrolysis or an inflammatory reaction during the process of being resorbed. This material has not enjoyed widespread use as a bone graft material containment system. Yet another drawback for bioresorbable materials is that acid generated by resorbable materials during degradation inhibits bone growth.

Thus, although using such a resorbable material may eliminate the need for a second surgical procedure, one general problem that may be experienced is an inflammatory reaction that is a necessary part of the resorption or degradation process associated with resorbable materials. Although a resorbable material does not need to be surgically removed, the body still has to remove it by hydrolysis or by metabolizing it, and this can cause problems.

Some procedures have used protein and/or growth factors, such as one or more bone morphogenic proteins (BMP), and bone graft material at a certain surgical site. In some instances, the protein and/or growth factor is deposited on a collagen matrix with a sponge-like quality. The protein and/or growth factor material adsorbs to the collagen sponge material. The collagen sponge is then placed in a site in the patient where the growth of additional bone is desired, either alone or mixed with another type of bone growth material, such as an allogeneic, autogenous, xenograft, alloplastic, or synthetic matrix.

Specifically, the implant material containing a growth factor is used to reconstruct areas where new bone growth is desired. For example, if the growth factor is BMP, the BMP attracts stem cells and induces them to convert to osteoblasts to make new bone. It is thus not necessary to exclude the invasion of fibrous or vascular tissue into the site, because the BMP will recruit stem cells from the soft tissue sites and convert them to bone. A vascular blood supply from the surrounding soft tissue is beneficial to the newly growing bone, so a membrane that excludes cells and vascular ingrowth is undesirable (and even potentially detrimental) to the process of growing new bone. If a barrier such as expanded (e)PTFE is used, it will not allow vascular access to the site from the surrounding tissues, and it must be removed at a later date, disrupting any peripheral vascularization that is supporting the new bone.

Many of the bone graft materials mentioned above are rigid and may have adequate compressive strength to resist collapse due to pressure from the overlying tissues and scar contracture during the healing process. However, other materials such as a collagen sponge treated with a protein and/or growth factor may not be resistant to compression, and will not adequately maintain the space for bone reconstruction unless protected by a supporting structure. Adequate protection may exist inside a tooth socket, but in the case of missing bone around the socket or missing portions of the alveolar ridge, a support structure is needed to keep the collagen sponge from collapsing. In short, these grafts, although inductive in nature, are not provided in forms that will maintain a desired shape. In addition, even bone graft materials with adequate compressive strength may be displaced by the forces exerted by the overlying tissue, or by forces from adjacent mobile structures such as the lips or tongue. Thus, there is a need for a space-maintaining support structure that does not require a second surgery for removal from the tissue.

Some surgeons use metal mesh, such as titanium mesh, for this purpose. They may also add autologous or cadaver materials, such as pieces of lamellar bone, to contain the collagen sponge or bone graft material and maintain the space for bone regeneration. Soft flexible membranes such as ePTFE are generally not stiff enough to accomplish this support function. Nor are resorbable membranes. One advantage of a titanium mesh is that it has relatively large openings to allow for vascular access to the implant material from the surrounding soft tissue. However, titanium mesh is somewhat bulky and has relatively sharp edges, which risks gingival irritation and eventual erosion through the overlying soft tissue and exposure to the oral cavity. Such exposure can be a nidus for the establishment of infective agents. Bone graft material may also extend through or migrate out of some of the mesh openings. Titanium mesh may also lack flexibility during surgery and it can be difficult for the surgeon to modify its size and shape during a procedure.

Even without exposure, the titanium mesh is often felt by the patient as an irregular surface beneath the gum tissue. It can also result in an unnatural appearance of the overlying tissue, because the pattern of the mesh may be visible or palpable under the overlying soft tissue. Also, the mesh is typically dark in color or anodized to have a bright or dark surface color, making it more visible through the overlying tissue. Therefore the mesh is often removed after the bone healing takes place, resulting in an additional surgical procedure, which increases costs and patient discomfort.

Other attempts to encourage bone growth during reconstruction have used bone induction trays, such as those described in U.S. Pat. No. 3,849,805 to Leake et al. and U.S. Pat. No. 4,636,215 to Schwartz. One of the problems with the Leake and Schwartz trays is that the voids or apertures that penetrate the trays are large. If this type of tray were to be used with certain implant materials, the tray may not sufficiently contain the material. Moreover, the thickness of the trays is necessary in order to support the mandible in use, but that resulting thickness may not be efficient enough at allowing vascular access to the bone graft material. The voids or apertures may also present the irregular surface and unnatural appearance problems described above.

In addition, the large flat surfaces and large open spaces associated with metal mesh may allow overlying tissues to move relative to the fixed mesh covering the bone graft site. Such movement disrupts the formation and penetration of new blood vessels into the bone graft site, and may cause tissue breakdown resulting in exposure of the metal mesh to outside contamination. Said movement may also lead to the formation of scar tissue at the tissue-metal mesh interface, reducing vascular access to the bone graft.

In a similar problem situation, soft and flexible materials such as GORE-TEX®, may allow the overlying tissues to move relative to the graft surface, resulting in tissue breakdown or excessive scar formation over the grafted site.

It is well known that many cell types do not express their phenotype or proliferate unless they have a surface to attach to and to grow on. When encouraging bone graft materials to stimulate bone growth, vascular tissue invading the bone graft is desirable to provide a blood supply to the bone graft. Thus a porous structure is desirable that has greater surface area than is provided by direct through holes in a containment material. A porous structure with a relatively random, omnidirectional interconnected pore structure, and which still maintains openings large enough to allow formation and passage of blood vessels through the pores and into the graft site, will provide greater surface area for the ingrowth of blood vessels and for the migration of bone forming cells into the site of desired bone formation. Such a relatively high surface area structure also helps to immobilize the overlying tissue due to the greater contact between the tissue and the structures surfaces and by initial ingrowth that integrates the overlying tissue into the many varied surfaces and openings presented by the material.

In short, previous attempts for bone grafting addressed only certain types of bone graft materials, and did not seek to provide solutions that could adequately contain and support a bone graft material that does not maintain its shape (for example, a sponge treated with a protein and/or growth factor, or a particulate bone graft material that is not placed in a protected area such as inside an extracted tooth socket). Additionally, for traditional bone grafts, the prior art methods used either a barrier-type soft and flexible membrane that does not allow vascular ingrowth (in order to isolate the bone graft material from the surrounding soft tissues) or a metal or alloplastic mesh or tray with large openings (which may allow the bone graft material to migrate out of the openings, may allow movement of the overlying tissue resulting in reduced neovascularization and greater scar formation, may present comfort and appearance problems including visibility through the overlying tissues once healing has taken place, may require a second surgery for removal, and are not as efficient at allowing or conducting vascular access to the graft site).

There is thus a need for a structure having a pore size sufficient to allow fibrovascular ingrowth, but small enough to contain bone graft materials in place in the structure, against the area where bone growth is to be encouraged. It is desirable for such a design to allow vascular ingrowth into the bone graft material, while maintaining the shape and space into which the bone graft material is placed. It is also desirable for such a material to be substantially or relatively smooth on the outside surface in order to allow soft tissue to be overlaid without irritation or tissue erosion and without the bone graft material containment structure being seen under the tissue once healed. It is also desirable for such a material to have an omnidirectional and/or multidimensional open pore structure large enough to provide for growth and penetration of new blood vessels, and with greater surface area than provided by straight through holes or openings in the containment structure. It is also desirable for such a material to be rigid enough to prevent collapse or displacement of a growth factor-treated collagen sponge alone or combined with other bone graft material. It is also desirable for such a material to be rigid enough to prevent collapse or displacement of a particulate bone graft material placed inside the containment structure due to tension from the overlying soft tissue closure or scar contraction. It is desirable for such a material to be rigid enough to prevent collapse or displacement of a bone graft material due to movement of adjacent structures such as the lips and tongue. It is also desirable that the implant does not have an adverse effect on the bone growth.

SUMMARY

The present inventors have designed a bone graft material containment structure that seeks to solve these and other problems. Embodiments of the present invention provide various biocompatible porous polymer containment structures for containing bone graft material. In one embodiment, these biocompatible porous polymer containment structures have interconnected pores. In one embodiment, these biocompatible porous polymer containment structures have omnidirectional, multidimensional, interconnected pores. These structures may be used for any bone graft materials that need containment. The containment structures may be formed into desired shapes by the health care professional before use. The desired shape depends on the specific application and anatomical site of desired bone growth. In another embodiment, the containment structures may be preformed into a tent, crib, trough, U-shape, pre-shaped sheet, or other shapes such as cylindrical, tubular, rectangular, square, ellipsoidal, box-shaped (e.g., a flat box or double sided thin box for cranial defects), or in the anatomical shape of any area of bone to be replaced or augmented in the body, or any other appropriate shape in order to hold and contain bone graft material in the desired location, such as against a bone defect to be treated to encourage new bone growth.

Various embodiments of the biocompatible containment structures may be designed of various types of materials, such as biocompatible polymers that have interconnected pore structures, thermoplastic resins, various types of polyethylenes (such as high density polyethylene (HDPE)), ultra high molecular weight polyethylene (UHMWPE), high molecular weight polyolefins, polyether ether ketone (PEEK), polyethylene terephthalate (PETE), nylon, polypropylene, or any polymer of aliphatic hydrocarbons containing one or more double bonds, composites of any of the above materials, or any other appropriate porous material that can be bent or otherwise formed into a desired shape. In one embodiment, the containment structure is made of sinterable thermoplastic resins having a low melt flow index. Different polymers have different definitions of melt flow index (MFI). For example, for polyethylene, the MFI should be below 2.0 g/10 minutes at 190° C. at a 2.16 kg load based on ASTM D1238. For polypropylene the MFI should be below 10.0 g/10 minutes at 230° C. at a 2.16 kg load based on ASTM D1238. For PEEK, the MFI should be below 10.0 g/10 minutes at 400° C. at 2.16 kg load based on ASTM D1238. In one embodiment, the containment structure is made of high density polyethylene. In another embodiment, the containment structure is made of ultra high molecular weight polyethylene. In yet another embodiment, the containment structure is made of polypropylene. Without limitation, the containment structure is made of any other biocompatible sinterable polymer, or a biocompatible metal, such as titanium, tantalum or surgical grade stainless steel.

In another embodiment, the biocompatible containment structures may be made of non-woven or woven webs made from polyethylene, HDPE, UHMWPE, polypropylene, PEEK or nylon. These biocompatible containment structures have a porosity (also called openness) between about 20 to about 60 percent and similar pore size ranges to other biocompatible containment structures described herein.

In another embodiment, the desired containment structure may be made using soluble solid displacement materials such as soluble salt or sugar granules placed in a mold and into which a liquid or plastic biocompatible polymer or metal is poured or injected, after which the soluble displacement material is leached or washed away. By controlling the size and shape of the displacement material, the resulting pores can be tailored to achieve the desired pore size, surface area and pore volume.

In another embodiment, a solid sheet or molded form may be mechanically drilled with various drill diameters at varied drill angles to provide a matrix of through holes that interconnect to form an omnidirectional open pore structure. The drill bit or the part may be rotated or translated in space during drilling to further vary the pattern and distribution of the pores. The same effect may be accomplished using various other techniques known to the art, such as laser ablation, water jet drilling or any other means appropriate to remove material from the solid sheet or molded form.

In another embodiment, the desired pore structure may be formed by various deposition processes known to the art, such as laser polymerized stereolithography, in which laser light is used to polymerize successive liquid polymer films to form a three dimensional interconnected porous structure, laser polymerized polymer powder in which successive layers of polymer granules are sintered by the energy of laser light (otherwise known as selective laser sintering), polymer deposition processes in which thin strands or droplets of molten or plastic polymer are selectively deposited in successive layers, thin film deposition in which successive thin films of material are layered and successively machined away, or any other deposition method of creating the desired pore structure.

In another embodiment, the desired pore structure may be formed by phase inversion polymerization, where a soluble polymer dispersed in a volatile solvent is mixed with another liquid with which it is insoluble, spread into a thin film, and where during evaporation of the volatile solvent the non solvent liquid coalesces into connecting droplets, leaving an open porous polymer structure surrounded by the non solvent liquid, which is then evaporated by heat or washed away by another volatile solvent.

Without restriction, any of the above methods, or any other method which produces an open pore structure with interconnecting open pore structure of appropriate pore size range, may be used to fabricate the bone graft material containment structures of the invention.

Without restriction, any of the above methods, or any other method which produces an open pore structure with omnidirectional, multidimensional, interconnecting open pore structure of appropriate pore size range, may be used to fabricate the bone graft material containment structures of the invention.

Various embodiments of the structures may have pore sizes ranging in average diameter size from about 40 to about 1000 microns, from about 100 to about 800 microns, from about 100 to about 500 microns, from about 50 to about 500 microns, from about 50 to about 500 microns, from about 60 to about 500 microns, from about 60 to about 400 microns, from about 200 to about 400 microns, from about 100 to about 200 microns, or pore sizes that are generally above about 100 microns, or pores that are generally about 200 microns. In another embodiment, the pore sizes are generally about 60 microns or greater.

Various embodiments of the containment structures may have thicknesses of about 0.1 to about 2.0 mm, about 0.1 to about 0.9 mm, about 0.1 to about 0.8 mm, about 0.2 to about 0.4 mm, about 0.2 to about 0.3 mm, or about 0.25 mm.

Various embodiments of the containment structures may be used to contain any type of bone graft material, such as autologous bone, autologous bone particulate, allogenic bone graft material (e.g., allogenic decellularized bone), human cadaver bone, xenograft bone graft material, animal bone, any type of bone chips or material, or synthetic materials or bone substitutes such as hydroxyapatite, calcium phosphate (such as tricalcium phosphate, synthetic hydroxyapatite, or coralline hydroxyapatite), ceramics, bioactive glass, calcium sulfate, polymer-based bone graft substitutes, growth factors that stimulate osteoblast precursors to proliferate, bone morphogenic proteins (BMP), BMP mimetics, recombinant human bone morphogenetic protein (rhBMP-2), platelet-rich plasma (PRP), transforming growth factor-beta (TGF-beta), platelet-derived growth factor (PDGF), such as recombinant human platelet derived growth factor (rhPDGF), insulin-like growth factors, fibroblast growth factors (FGF), xenographic bone proteins, growth differentiation factor (e.g., GDF5), calcitonin, calcitonin mimetics, Curasan Cerasorb® synthetic beta tricalcium phosphate (Curasan AG), Medtronic INFUSE® Bone Graft (Medtronic, Minneapolis, Minn.), marrow cells containing mesenchymal stem cells, bone marrow aspirate, and any other appropriate bone graft materials, used alone or in combination. Such materials will generally be referred to as "bone graft material" throughout this specification, and any types of the bone graft materials described herein are intended for use with the bone graft material containment structures described herein. Various embodiments of the structures may be used any time a surgeon treats a bone fracture or defect and wishes to encourage new bone growth at the treated site.

Other embodiments relate to methods for securing bone graft material containment structures in place. Methods of securing such materials to the body are generally known to one of ordinary skill in the art. In different applications, staples, tacks, sutures, orthopedic nails, surgical wire, adhesive and/or glue may be employed. For example, the structures may be positioned near the bone defect, filled with bone graft material, and secured closed or otherwise secured to the surgical site. Soft tissue may then be placed over the structure and secured for the healing and bone formation process.

BRIEF DESCRIPTION OF THE FIGURES

FIG. 10A is a view from above while FIG. 10B shows a cross section of the bone graft material containment structure having the spacer feature.

DETAILED DESCRIPTION

Figure 1:
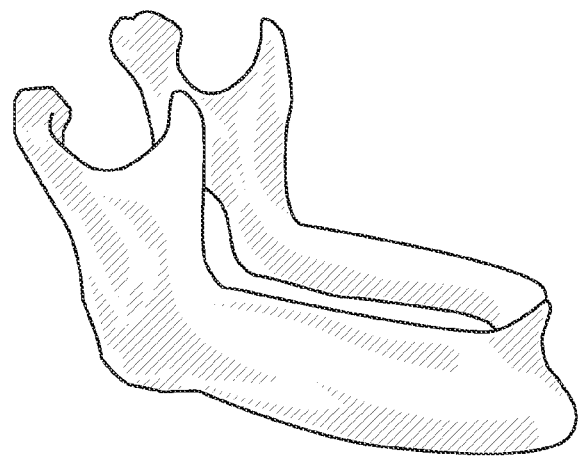
FIG. 1 shows a side perspective view of a normal mandible (without teeth).

Various embodiments of the present invention provide bone graft material containment structures designed to be used in connection with bone graft materials, including proteins and/or growth factors. The structures are designed to contain bone graft material in place, as well as maintain the tissue space shape and form required for the bone graft. The structures may be provided in sheets that can be cut and that have specific features to enable their use as bone graft material containment structures. The structures may be provided in a pre-formed shape and then further shaped or cut by a surgeon to a specific desired shape. The structures may be provided in semi-custom or custom forms.

Various embodiments of the designs described are useful in a number of bone repair applications. Bone repair is generally intended to treat defects due to trauma, congenital defects, malignant diseases that affect bone (such as various cancers), periodontal disease, or for a multitude of other reasons. In certain bone repair surgeries, the surgeon may wish to encourage the growth of new bone in addition to or instead of repairing the damaged bone. This may be the case with any type of bone repair surgery, for example, in the craniofacial area, the pelvis, the spine, the thorax, any of the long bones (such as the femur, tibia, humerus), or any smaller bones (such as the bones of the ankle, fingers, or toes). It is envisioned that the devices and methods described herein may be used to contain any type of bone graft material against any bone of the skeleton, and particularly, the appendicular skeleton.

For example, one embodiment may be used in treating or repairing craniofacial bone that is deficient or missing, such as repair of a cranial bone defect or maxillofacial bone defect. Typical maxillofacial surgery applications include but are not limited to surgery to correct the mandible, maxilla, or alveolar ridge in order to establish new bone to support dental implants or dentures. Other applications may include treating spinal bone defects or spinal fusion procedures where bone is induced to grow between vertebrae. Further applications include treating comminuted fractures. Further applications include treatment of the bones of pelvis. For ease of reference, facial applications will be discussed in more detail below, but it should be understood that the methods and devices described herein are not limited to these surgical uses.

Embodiments of the invention relate to bone graft material containment structures designed to contain bone graft materials. Bone graft materials are known to one of ordinary skill in the art. Non-limiting examples of potential bone graft materials include autologous bone, autologous bone particulate, allogenic bone graft material (e.g., allogenic decellularized bone), human cadaver bone, xenograft bone graft material, animal bone, any type of bone chips or material, or synthetic materials such as hydroxyapatite, calcium phosphate (such as tricalcium phosphate, synthetic hydroxyapatite, or coralline hydroxyapatite), ceramics, bioactive glass, calcium sulfate, polymer-based bone graft substitutes, or growth factors that stimulate osteoblast precursors to proliferate, bone morphogenic proteins (BMP), BMP mimetics, recombinant human bone morphogenetic protein (rhBMP-2), platelet-rich plasma (PRP), transforming growth factor-beta (TGF-beta), platelet-derived growth factor (PDGF), such as recombinant human platelet derived growth factor (rhPDGF), insulin-like growth factors, fibroblast growth factors (FGF), xenographic bone proteins, growth differentiation factor (e.g., GDF5), calcitonin, calcitonin mimetics, Curasan Cerasorb®, Medtronic INFUSE® Bone Graft (Medtronic, Minneapolis, Minn.), marrow cells containing mesenchymal stem cells, bone marrow aspirate, and any other appropriate bone graft materials, used alone or in combination. Such materials will generally be referred to as "bone graft material" throughout this specification, and any types of the bone graft materials described herein are intended for use with the bone graft material containment structures described herein.

The proteins and/or growth factors described may be used in addition to or in place of autologous, allogenic, xenograft, or synthetic bone graft materials. In a specific embodiment, a protein and/or growth factor that has been adsorbed onto a sponge-like or soft material (referred to as a "treated sponge" throughout the remainder this application) may be used. The sponge-like or soft material may be any appropriate carrier that can support and adsorb a protein and/or growth factor, one non-limiting example of which includes a collagen sponge.

The treated sponge may be treated with any type of material that is designed to encourage or stimulate bone growth. Non-limiting examples of appropriate proteins and/or growth factors that may be used in connection with the embodiments described include the above-described bone graft materials, and specifically may include growth factors that stimulate osteoblast precursors to proliferate, bone morphogenic proteins (BMP), BMP mimetics, recombinant human bone morphogenic protein (rhBMP-2), platelet-rich plasma (PRP), transforming growth factor-beta (TGF-beta), platelet-derived growth factor (PDGF), such as recombinant human platelet derived growth factor (rhPDGF), insulin-like growth factors, fibroblast growth factors (FGF), xenographic bone proteins, growth differentiation factor (e.g., GDF5), calcitonin, calcitonin mimetics, Curasan Cerasorb®, Medtronic INFUSE® Bone Graft (Medtronic, Minneapolis, Minn.), marrow cells containing mesenchymal stem cells, bone marrow aspirate, and any other appropriate bone growth factors or proteins that stimulate bone production or combinations thereof.

The improved bone graft material containment structures and methods described herein are particularly designed to retain bone graft materials and to maintain the space where bone is to be restored during the bone healing process. The material of the structure should be biocompatible, and may be any appropriate tissue-integrating or porous polymer, or other biocompatible material. Examples of potential materials are biocompatible polymers that have interconnected pore structures, thermoplastic resins, various types of polyethylenes (such as high density polyethylene), ultra high molecular weight polyethylene (UHMWPE), polyolefins, polyether ether ketone (PEEK), polyethylene terephthalate (PETE), nylon, polypropylene, or any polymer of aliphatic hydrocarbons containing one or more double bonds, composites of any of the above materials, or any other appropriate porous material that can be bent or otherwise formed into a desired shape. In one embodiment, the containment structure is made of high density polyethylene. In another embodiment, the containment structure is made of ultra high molecular weight polyethylene. In yet another embodiment, the containment structure is made of polypropylene. Biocompatible metals include but are not limited to surgical grade stainless steel, tantalum and titanium. In one embodiment, these metals may be sintered to make the porous bone graft material containment structures. In another embodiment, multiple layers of metal mesh or metal wire are sintered together to make the porous bone graft material containment structures.

In another embodiment, the biocompatible containment structures may be made of non-woven or woven webs made from polyethylene, HDPE, UHMWPE, polypropylene, PEEK or nylon. These biocompatible containment structures have a porosity (also called openness) between about 20 to about 60 percent and similar pore size ranges to other biocompatible containment structures described herein.

In one embodiment, the structure is substantially or relatively smooth on the outside surface, such that the surface helps prevent snagging of soft tissue over the structure, tissue erosion, or irritation to the patient. The smoothness also contributes to relative external invisibility post-healing.

The material of the structure has pores that are sized to allow vascular access to the bone healing site, but small enough to maintain the bone graft material in place against the defect to be treated, and have generally an interconnected open pore structure, generally consisting of various pore sizes within a desired size range distributed throughout the material. In some embodiments, this pore structure is omnidirectional and/or multidimensional. The term multidimensional signifies pores of different sizes within a desired size range. The term omnidirectional signifies that the pores are oriented in many directions within the porous material. An example is provided in FIG. 9. In a specific embodiment, the structure is formed of a material having a porous structure, with pores in the range of about 40 to about 1000 microns in average diameter. In another embodiment, the pores may range from about 100 to about 800 microns in average diameter. In another embodiment, the pores may range from about 100 to about 500 microns in average diameter. In another embodiment, the pores may range from about 50 to about 500 microns in average diameter. In another embodiment, the pores may range from about 60 to about 400 microns in average diameter. In another embodiment, the pores may range from about 200 to about 400 microns in average diameter. In a further embodiment, the pores may be generally between about 100 to about 200 microns in average diameter. In an even further embodiment, the pores may be generally above about 100 microns. In an even further embodiment, the pores may be generally about 200 microns. In an even further embodiment, the pore sizes are generally about 60 microns or above. Generally, pore sizes above about 60 microns allow blood vessels to grow into and through the material. It is contemplated that any numerical pore size or pore size range within these stated ranges can be used.

Generally, there may be variation in pore size, such that some pores are as small as about 10 or 5 microns, with other pores being much larger. The averages given above are intended to be examples of various average pore size ranges throughout the material. Due to the interconnected pore structure of the desired material used, the pore sizes are somewhat irregular, providing a number of variously sized surfaces to encourage fibrovascular ingrowth and integration. One example of a material having the above-described properties is MEDPOR® manufactured by Porex Surgical Products Group (Newnan, Ga.) and is shown in FIG. 9.

The addition of proteins and/or growth factors (such as BMP) or bone proteins supplied by graft materials (such as cancellous bone from the patient's body, or from some external source like bone allograft) will form bone, but only if it has access to a blood supply. Guided tissue regeneration using barrier materials may be sufficient for small defects in direct contact with freshly bleeding bone, however, larger defects need a blood supply through the bone graft containment material. Thus, it is desired for the pore sizes of the bone graft material containment structures described herein to be adequate to allow fibrovascular infiltration and vascularization of the bone graft material contained within the bone graft material containment structure.

In certain embodiments, it is desirable to provide adequate pore volume to allow rapid vascularization to the site from the surrounding soft tissues, but small enough that the pores may contain specific types of bone graft materials without immediate leaching.

Figure 9:
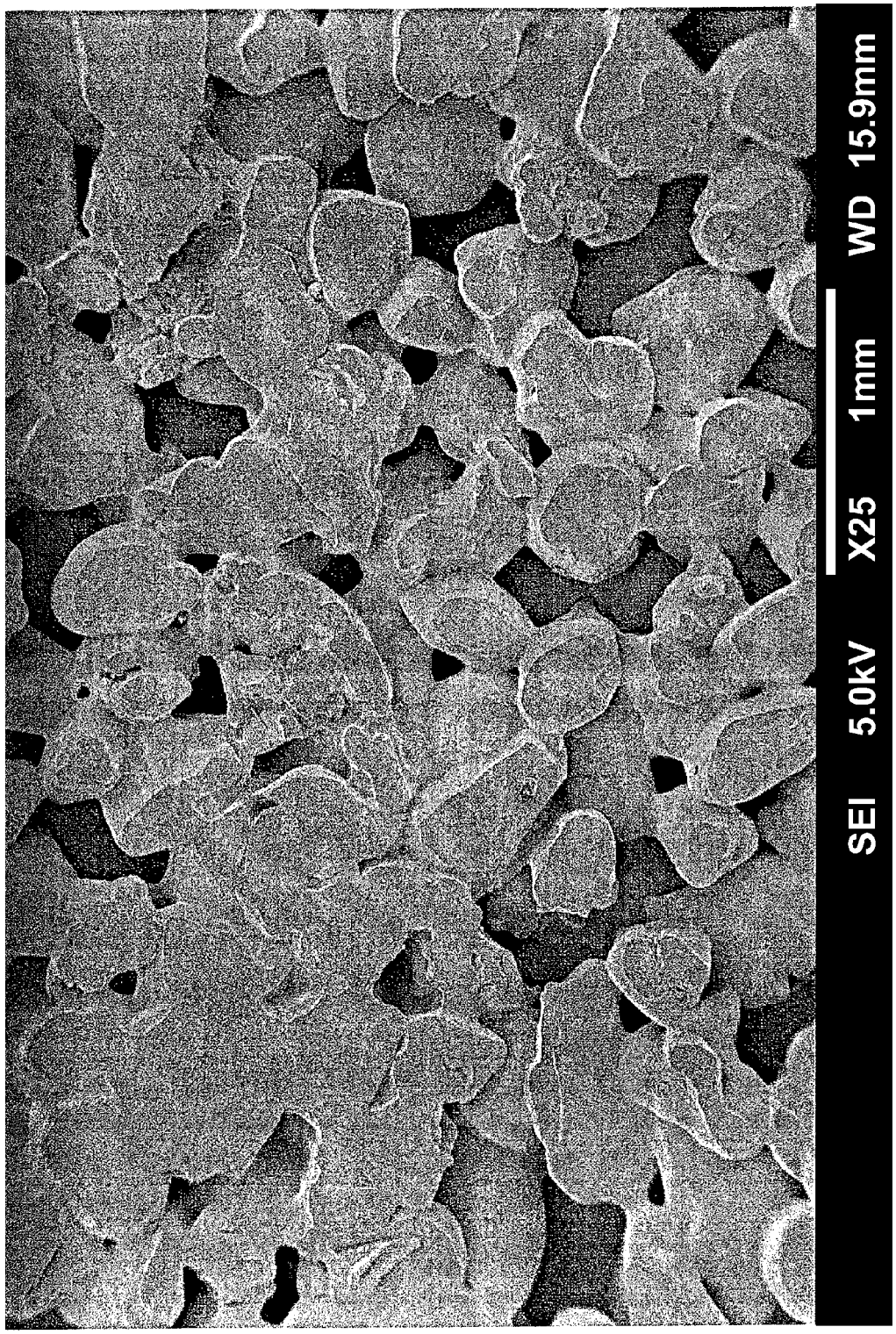
FIG. 9 shows a scanning electron micrograph (SEM) of the material of a bone graft material containment structure according to one embodiment, showing an omnidirectional pore structure. This embodiment is a 0.25 mm thick sheet of MEDPOR shown at a magnification of 25× (MEDPOR® manufactured by Porex Surgical Products Group (Newnan, Ga.).

The pores are also typically provided in an interconnected omnidirectional pore structure, an example of which is shown in FIG. 9. This is a scanning electron micrograph of a 0.25 mm thick sheet of MEDPOR shown at a magnification of 50× (MEDPOR® manufactured by Porex Surgical Products Group (Newnan, Ga.). In one embodiment, this pore structure provides high internal surface area and high pore volume relative to the pore size. In other words, rather than providing straight through-pores, or a uniform pore structure provided by a mesh design, various embodiments of the present invention provide a pore structure that is irregular and omnidirectional. This provides many surfaces for vascular tissue ingrowth through the bone graft material containment structure and into the graft site.

The interconnecting porous structure provides a number of benefits. First, the structure does not have to be hydrolyzed (as with the resorbable membranes), nor does it have to be removed. The pore structure conducts fibrovascular tissue to the bone regeneration site by way of its large surface area and accommodating pore size. Second, the larger surface area associated with this pore structure is a benefit over the bone induction trays of the prior art. For example, although the Leake tray shows large holes through the tray that will allow fibrovascular tissue to access the bone material, the interconnected omnidirectional pore structure described and shown herein provides more surfaces to direct the fibrovascular tissue to the bone graft site. Cells need a surface on which to grow. The greater surface area provided by the omnidirectional pores of the described bone graft material containment structures provides additional surfaces for cell proliferation and vascular ingrowth as compared to the prior art designs.

The described irregular open pore structure also provides for tissue integration, or tissue attachment and stabilization relative to the containment material. This tissue integration minimizes movement of the overlying tissue during the initial healing phase and thereafter. The tissue integration is beneficial to rapid healing because movement of the tissue relative to the graft containment material can disrupt the formation of new vessels and lead to scar tissue, minimal vascularization of the bone graft material and tissue breakdown over the graft.

The bone graft material containment structures provided are also rigid or inherently stiff enough to prevent collapse due to tension from the overlying soft tissue closure or scar contraction. At the same time, they are also thin enough to have sufficient flexibility to be adapted or bent to fit the specific surgical site for the purpose of holding the space open for a bone graft material, while allowing rapid vascular access from overlying soft tissue to the bone regeneration site through the porous structure.

Figure 4:
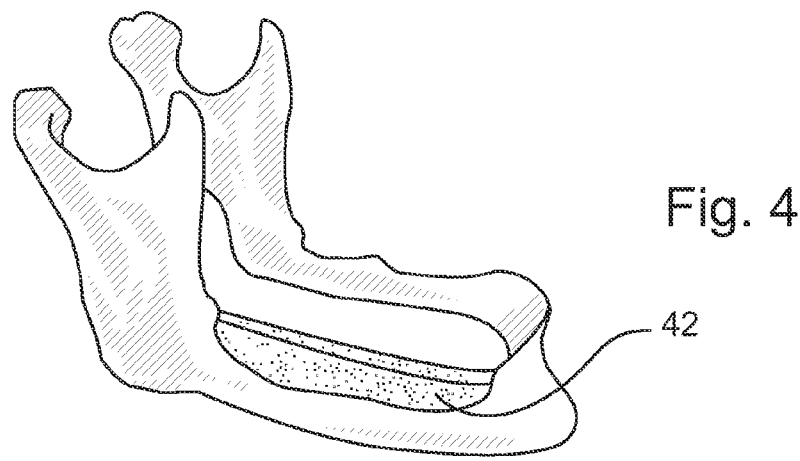
FIG. 4 shows a side perspective view of the design of FIG. 3 in place in a patient's mandible.

The general function of the structure is to contain and support bone graft material. In a specific embodiment, one type of bone graft material that may need a specific support is a treated sponge, such as a collagen/BMP sponge. In another embodiment, a bone graft material such as beta tricalcium phosphate granules require containment at a desired site. The bone graft material containment structures, however, are not intended to provide the rigidity necessary to support the mandible during the healing phase, as some of the prior art trays described above must do. In fact, for some uses in the mandible or maxilla, a titanium plate is needed to stabilize the entire reconstructed area of the bone during the healing process, as shown by FIG. 4. By contrast, the prior art bone induction trays described above are designed to have an initial rigidity similar to the mandible bone itself and must be thick enough to provide that structural rigidity.

In a specific embodiment, the bone graft material containment structures are formed of a sheet material having a thickness of about 0.1 to about 3.0 mm, about 0.1 to about 2.0 mm, about 0.1 to about 1.0 mm, about 0.1 to about 0.9 mm, about 0.1 to about 0.8 mm and in another embodiment, a thickness of about 0.2 to about 0.4 mm. In another embodiment, the thickness is about 0.2 to about 0.3 mm, and in another embodiment, the thickness is about 0.25 mm. It is contemplated that any numerical thickness within these stated ranges can be used. In some cases the material may be thin in some areas and thicker in other areas to confer additional strength to the material where needed.

By providing the porous material in a very thin design, for example, between about 0.1 to about 1.0 mm thick, and in more specific embodiments, about 0.2 to about 0.5 mm thick, and by providing an open omnidirectional pore structure with pores that are sized in the above-described ranges, the desired fibrovascular ingrowth and blood vessel ingrowth can be obtained. In short, the irregular morphology of the pores, as well as their sizes provide more surfaces to direct fibrovascular ingrowth and thus vascular supply into the bone graft material containment structure, while still supplying the space maintenance feature to keep the bone graft material in the desired shape and location to establish new bone.

The sheet may be provided in a general approximate shape and size of the anatomical region of use. The material can then be cut to size by the surgeon, bent by hand to cover a surgical site containing bone graft material, and, if necessary fixed into the site with surgical tacks, screws, sutures or other means.

One specific example of a material that may be used to form the bone graft material containment structures described herein is MEDPOR® Biomaterial provided by Porex Surgical Products Group (Newnan, Ga., USA). The MEDPOR® surgical implants are manufactured from linear high-density polyethylene. The material allows for tissue ingrowth because of its interconnecting open pore structure, an example of which is shown in the attached FIG. 9. Specifically, the pores are provided in an omnidirectional interconnecting pore structure, with an average pore size greater than about 100 microns. The pore volume may be greater than about 10%, greater than about 15%, greater than about 20%, or greater than about 30%. In different embodiments, the pore volume may range from about 10% to about 60%, from about 20% to about 60%, from about 30% to about 60%, or from about 40% to about 50%. In some embodiments, the pore volume may be about 50% in further embodiments. Such assessments of pore volume may be made by one of ordinary skill in the art using mercury intrusion porosimetry measurements or using direct measurements of pores in micrographs, such as SEMs.

The firm nature of the material allows carving with a variety of sharp surgical instruments without collapsing the pore structure. In other embodiments, the bone graft containment material has a thickness of about 0.25 mm, about 0.35 mm, about 0.45 mm, or about 0.85 mm, all with average pore sizes of about 200 microns. In another embodiment of the invention, larger through holes of approximately 1 mm to 2 mm diameter may be added to allow faster vascularization into the underlying bone graft material. These through holes would not replace the porosity of the omnidirectional open pore structure of the rest of the containment structure.

In another embodiment, the containment structure has metal or other reinforcement in mesh or rebar form. In another embodiment of the invention, the porous structure has metal wires embedded in a polymer structure for reinforcement, or short elongated metal strands located throughout the structure to provide additional support and help the material hold its shape when bent.

In yet another embodiment, the containment structure has collagen integrated into the porous containment structure or onto the surfaces of the containment structure. In this embodiment, the collagen attached to the surfaces of the containment structure can serve as a carrier for growth factors such as rhBMP. In a similar embodiment, the attached collagen includes a porous collagen layer approximately 0.1 to 1.0 mm thick on the soft tissue side of the containment structure. This porous collagen layer provides a soft but stable support structure for fibrovascular ingrowth into the bone graft material, while adding bulk to the overlying tissue, and further minimizing the chance for erosion of the containment structure through the overlying tissue. Collagen may be integrated into or onto the porous containment structure using methods known to one of ordinary skill in the art, including preparing a suspension of collagen fibers and filtering the collagen fibers through the porous containment structure followed by drying. Different forms of collagen may be used.

The present inventors have found that MEDPOR® surgical implants may be manufactured in a wide variety of shapes and sizes for use as bone graft material containment structures for reconstructive surgery. Specifically, the material for containment structures may be provided as sheets or as pre-formed shapes intended to align with the desired bone contour. The properties of the MEDPOR® material allow it to be cut and trimmed while maintaining the interconnectivity and the structure of the pores. They may also be provided in custom or semi-custom shapes.

Figure 3:
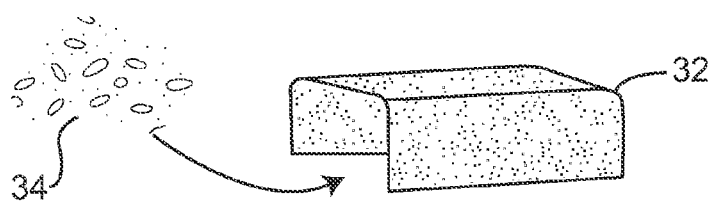
FIG. 3 shows a side perspective view of one embodiment of a bone graft material containment structure having a preformed porous polymer tent shape designed to hold and contain bone graft material.
Figure 7:
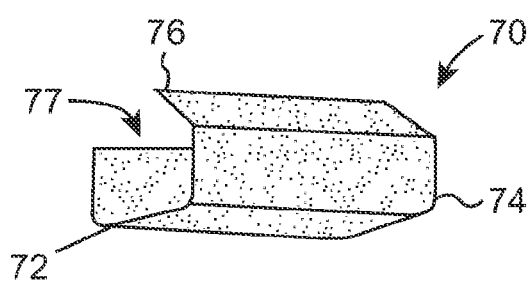
FIG. 7 shows a side perspective view of one embodiment of a bone graft material containment structure having a preformed open pore structure crib designed to hold and contain bone graft material.
Figure 12:
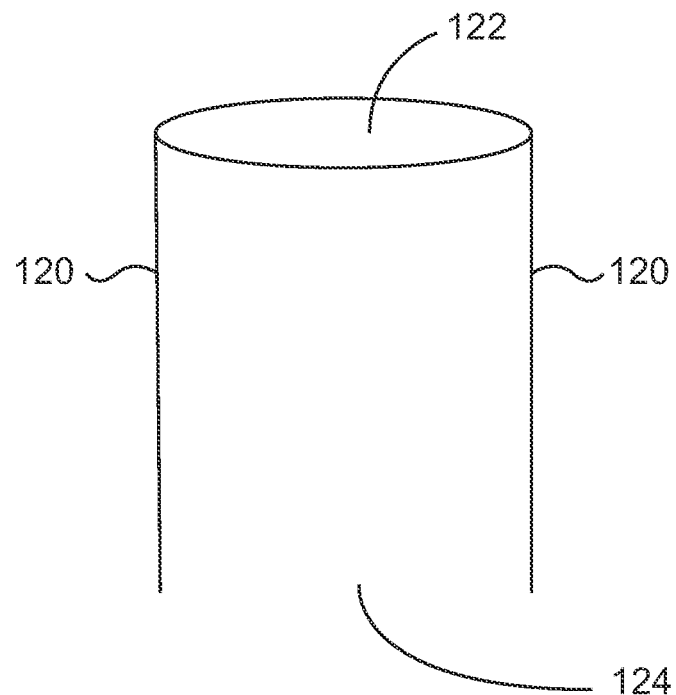
FIG. 12 shows a side view of one embodiment of a bone graft material containment structure having a cylindrical shape with an open lower portion.

The attached figures show various examples of potential bone graft material containment structure shapes. For example, FIG. 3 shows an embodiment in which the structure is preformed in a tent-like shape to hold bone graft material in place against the defect to be treated. FIG. 7 shows an embodiment in which the structure is hinged or creased at the top to provide a container or crib for the desired material. Although not shown, another potential embodiment is to leave out the "lid" from FIG. 7 and provide the bone graft material containment structure in a trough-like or U shape. FIG. 12 shows an embodiment in which the structure is cylindrical with an open end in order to contain bone material within the cylinder and allow the material to contact bone at the bottom of the cylinder. The structures are also generally intended to be provided in various lengths and sizes. In one embodiment, the structures are shaped like a tooth-whitening tray, which can be used to treat a patient with periodontal disease.

Figure 10:
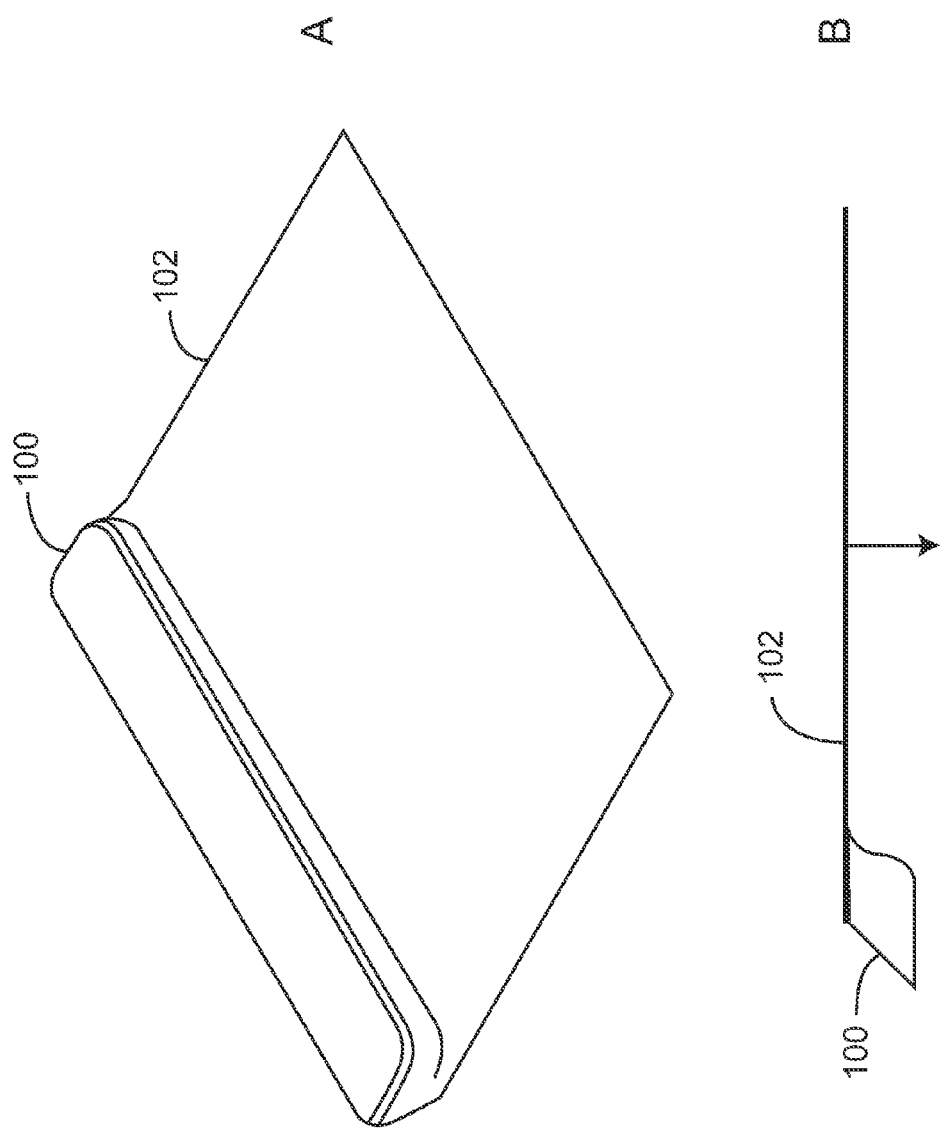
FIG. 10 shows two views of one embodiment of a bone graft material containment structure having a spacer feature.
Figure 13:
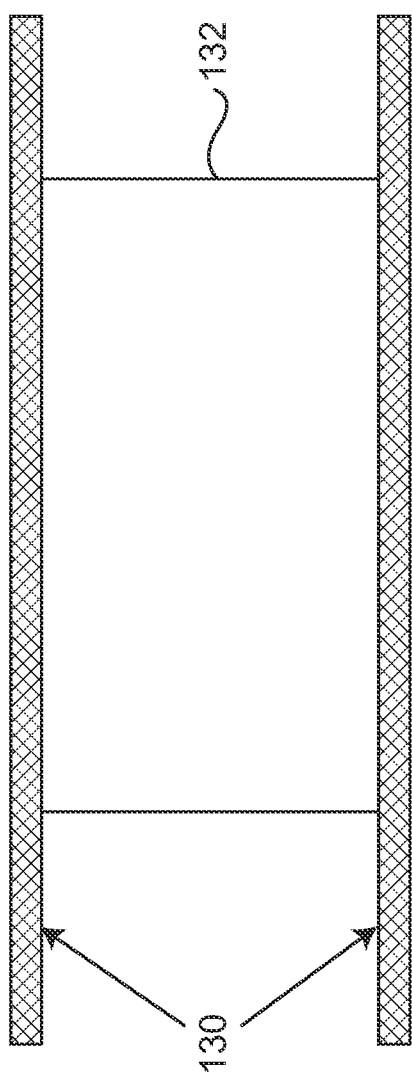
FIG. 13 is a schematic representation of a porous plastic containment sheet 130 located on two sides of a bone morphogenic protein containing media 132 (BMP media).
Figure 14:
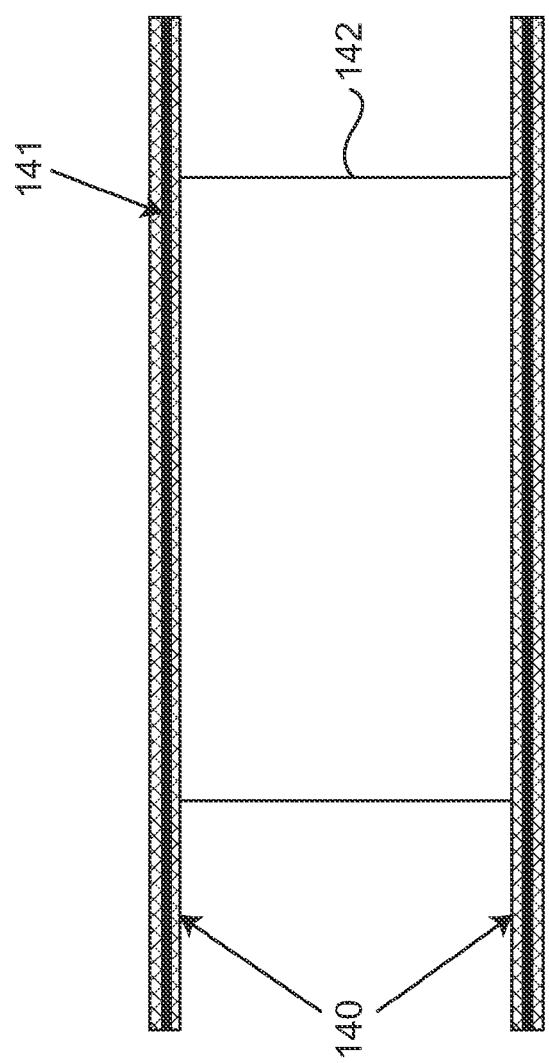
FIG. 14 is a schematic representation of a porous plastic containment sheet 140 containing a metal mesh 141, the sheet being located on two sides of a bone morphogenic protein containing media 142 (BMP media).

The structures may alternatively be provided as a sheet-like material that can be secured to existing bone and wrapped around or spanned over the bone graft material and secured to a second surface to create, for example, a sling-like or bridge-like design. FIGS. 11 and 13 show an embodiment in which the bone graft material containment material is provided as a sheet-like form. The structures may also be provided having a spacer bar, as illustrated in FIGS. 10 and 11, described further below.

Figure 2:
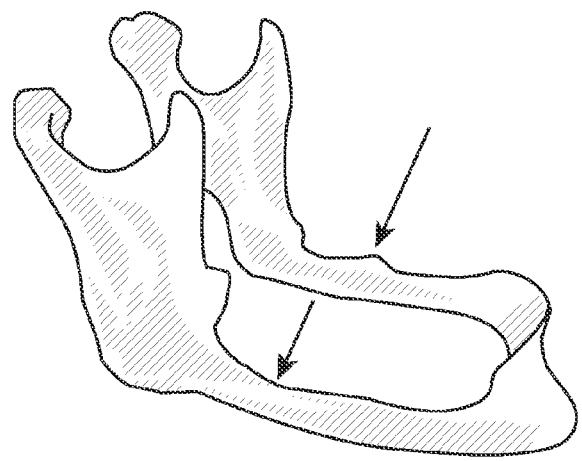
FIG. 2 shows a side perspective view of a mandible with bone deficiencies.

Referring now more specifically to FIGS. 1-8, FIG. 1 shows a normal, healthy mandible (without teeth). FIG. 2 shows a diseased or damaged mandible, which could occur, for example, from bone resorption, excision of diseased bone, a trauma to the face, or for any other reason. The arrows in FIG. 2 indicate areas of bone loss. FIG. 3 shows one embodiment of a bone graft material containment structure 32 that is provided in a tent-like shape to hold bone graft material 34. The structure 32 has side portions, a top portion and an interior portion into which bone graft material 34 is placed as indicated by the arrow. The structure may then be sutured, tacked, screwed, or otherwise positioned into place against the portion of the patient's bone defect to be treated. Soft tissue may be closed over the bone graft material containment structure. FIG. 4 shows the bone graft material containment structure 42 containing the bone graft material (not shown) located in position on the mandible.

Figure 5:
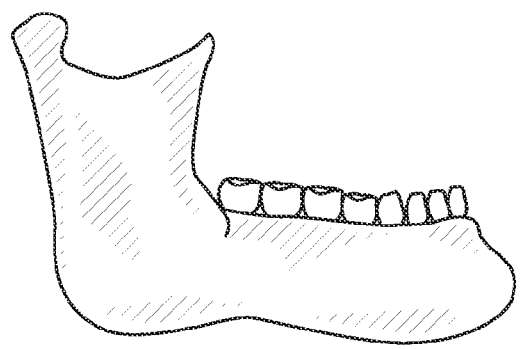
FIG. 5 shows a side view of a normal mandible (with teeth).
Figure 6:
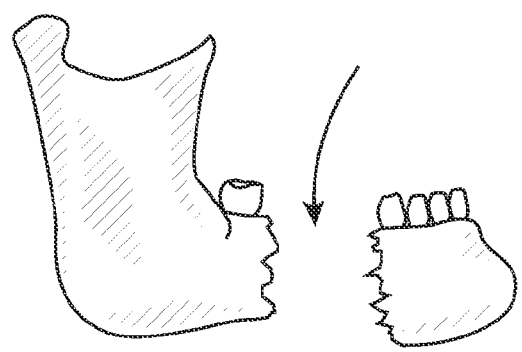
FIG. 6 shows a side view of a mandible with a portion of bone removed.
Figure 8:
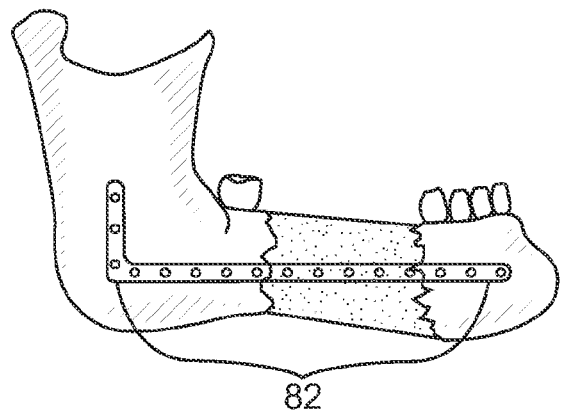
FIG. 8 shows a side view of the design of FIG. 7 in place in a patient's mandible, along with a bone plate stabilizer to stabilize the bone during healing.

FIG. 5 shows a normal, healthy mandible (with teeth). FIG. 6 illustrates a mandible having a portion of the bone removed (arrow), for example, due to excision of a tumor or removal of cancerous bone, a congenital defect, or for any other reason. FIG. 7 shows one embodiment of a bone graft material containment structure that is provided in a crib-like shape 70 to hold bone graft material. The structure has a lower portion 72, side portions 74, a top "lid" portion 76, and an interior portion 77 into which bone graft material is placed. The structure is shown having rounded sides, but it may be provided with more angled sides if desired, depending upon the intended use. FIG. 8 shows a side view of the bone graft material containment structure that is provided in a crib-like shape shown in FIG. 7 in place in a patient's mandible, along with a bone plate stabilizer 82 to stabilize the bone during healing. Following bone growth and healing, dental implants can be placed in the newly formed bone. The bone plate (such as a titanium bone plate with openings 82) may be secured into place in order to bridge the missing portion of the mandible. The structure may then be sutured, tacked, screwed, or otherwise positioned into place against the portion of the patient's bone defect to be treated. Soft tissue may be closed over the bone graft material containment structure.

In certain embodiments, the bone graft material containment structure may be provided as a bone graft containment sheet that accommodates an upper tack portion, a middle wrap portion, and a lower tack portion which can be shaped by the surgeon by affixing it to the bone or soft tissues at the desired site. Following the fixation of one side of the sheet, the bone graft material may be added to the sheet which wraps around it and the second edge of the sheet is then affixed into place. In other embodiments, the bone graft material containment structure may be provided as a bone graft containment sheet having a predetermined shape that accommodates an upper tack portion, a middle wrap portion, and a lower tack portion. In other embodiments, the structure is provided pre-formed into the shape of various potential and expected bony defect sites. In these embodiments, the compound curves of these specific shapes may lend additional stiffness to the thin, preformed shape. As discussed above, examples of such shapes may be tented shapes (for example, to cover and augment the alveolar ridge), trough shapes (for example, to support collagen sponge material to replace missing portions of the mandible), and anatomic shapes to augment craniofacial bone. Further options are to provide the bone graft material containment structures in forms that are shapes such as cylindrical, tubular, rectangular, square, ellipsoidal, box-shaped (e.g., a flat box or double sided thin box for cranial defects), or in the anatomical shape of any area of bone to be replaced or augmented in the body, or any other appropriate shape in order to hold and contain bone graft material in the desired location, such as against a bone defect to be treated to encourage new bone growth. It is also envisioned that the bone graft material containment structures may be custom shaped.

Figure 11E:
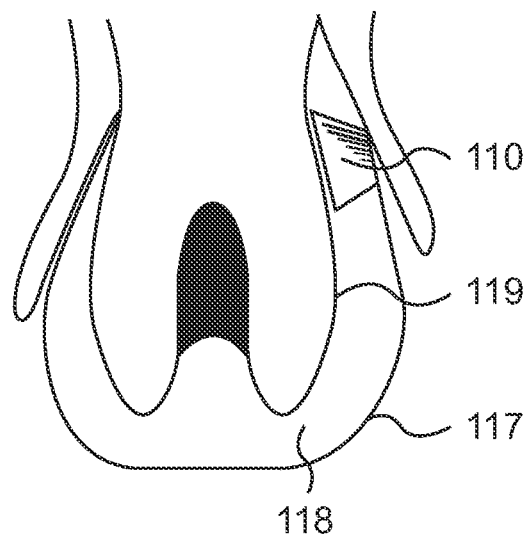
FIGS. 11 A-E show the structure of FIG. 10 being shaped by a surgeon and being positioned in the patient.

FIG. 10 shows an example of a bone graft material containment structure that has a spacer portion. FIG. 10A provides a view from above. FIG. 10B shows a cross section. The spacer portion design is essentially a bone graft material containment sheet with a "space bar" 100 on one end of the sheet 102 that is provided in order to maintain space on the maxilla or mandible using the technique described above for augmenting bone on the mandible or maxilla. It is usually placed on the labial side of the bone and allows the surgeon to create extra room for bone formation to support the dental implant. The arrow in FIG. 10B shows the side of the sheet which is applied to the bone. Specifically, it can be cut so that it feathers to the basal bone and then extends to maintain space for the graft. An example of this is shown in FIG. 11, which illustrates the space bar 110 having its edges 112, 114 cut away or shaved (e.g., with a scalpel) at an angle (or "feathered") so that there is a raised area in the middle portion 116 with wedge-shaped shaved edges, as shown in FIGS. 11C-D. This raised area raises the rest of the sheet up against the desired surface in order to provide additional space underneath the sheet (between the bone and the sheet). The raised area 110 holds the sheet away from the bone so that more bone graft material can be inserted underneath the sheet. The sides of the sheet portion 116 (the portions below the area where a wedge-shaped portion of material has been removed) can then be pressed or otherwise secured down to contain the bone graft material in a bed-like area in the desired location 118. The raised area acts as a "raised pillow" and the remaining lower portion of the sheet 117 provides a "cover" for the bone graft material. In essence, this embodiment gives the surgeon the option of encouraging bone growth on a labial surface of the bone 119, as shown for example in FIG. 11E. In the instance of a dental application, it may be useful to encourage bone growth not only in the tooth socket area of the maxillary bone 113, but also near the labial surface of bone 119. The space bar portion may have the above-described pore structures or it may be more solid-like. The step of the space bar portion may be about 2 mm to about 3 mm, although any dimensions are possible, depending upon the specific use and anatomy to be treated.

FIG. 12 shows one embodiment of a bone graft material containment structure that is provided in a cylindrical-like shape to hold bone graft material. The structure is shown as having rounded sides 120, a closed upper portion 122, and an open lower portion 124. The closed upper portion 122 may be provided as a lid that may be opened and optionally secured closed, or that it may be provided pre-sealed. Bone graft material may be placed against the bone in the open end. This embodiment can be particularly useful for encouraging bone growth in the oral cavity, e.g., in the location of a missing tooth.

Options for treating other bones include bone cages for spinal fusion procedures, tubular or semitubular shapes for appendicular defects, (long bones), and bone/implant interface areas such as for artificial joints. Other options include bone graft material containment shells for cosmetic or reconstructive bone onlay grafts such as for the midface, chin, nose, or periorbital area. Embodiments may also be used for repair of craniotomy defects, full or partial thickness defects of the cranium due to trauma, cancer resection, or lost bone flaps after procedures on the brain.

In one embodiment, the structure is molded into a shape to augment any desired bone, for example the cranium, craniofacial bones, the spine, the scapula, the ribs, the humerus, the radius, the ulna, bones of the wrist, the phalanges, the pelvis, the coccyx, the femur, the tibia, the fibula, bones of the foot or ankle, or any other bone.

In a further embodiment, the structure is molded into a shape to augment existing craniofacial bone, including but not limited to the mandible, maxilla, palatine bone, zygoma or the frontal, parietal, occipital or temporal bones.

In an alternate embodiment for use on other skeletal bones, the material may be molded into a shape to contain bone graft material over or within a bony defect of the long bones, such as for a poorly healing or comminuted fracture.

In another embodiment, the material may be molded to the shape of a particular defect for a particular patient, utilizing CT or MRI data or a physical impression of the defect area.

In a further embodiment, the sheet or molded shapes have attached extensions or spacer bars to hold the sheet or molded shape away from the existing bone surface, in order to provide additional space for the bone graft material to establish new bone.

In another embodiment, thicker ribs of thermoplastic or another material may be incorporated into the material for added strength.

In another embodiment, stiffening agents are provided to increase the strength, such as biocompatible fibers or metal rods inside the polymer material, outside the polymer material, and/or both. Stiffening agents may include titanium wire, titanium rods, biocompatible polymer solid rods or fibers, polymer mesh, or any other appropriate stiffening materials.

In another embodiment, a metal mesh may be molded into the material so that the porous material surrounds the metal mesh and fills the interstices of the metal mesh or plate to provide support to the bony defect area while the bone heals. An example of molding of a porous material over a metal mesh is described in U.S. Pat. No. 7,655,047 and in co-pending application Ser. No. 11/445,560.

A specific method of manufacturing materials that may be used to provide certain bone graft material containment structures will now be described. It should be understood, however, that this manufacturing method is intended to be illustrative in nature and is not limiting to the present invention. Various modifications are also envisioned. In one manufacturing embodiment, small particles of a polymer, such as polyethylene or polyethylene fines, are introduced into a mold (which is pre-shaped into the desired bone graft material containment structure shape). The small particles are then sintered together under heat and pressure. This provides a material or matrix having an interconnected pore structure. Various examples of methods of making a material suitable for use in connection with the present invention are described in U.S. Pat. No. 7,655,047 and in co-pending application Ser. No. 11/445,560.

An alternate method for manufacturing various implants is to coin curves into a flat sheet (such as a flat polyethylene sintered sheet) for improved anatomic shapes. This is particularly useful because it may be easier to make material as a flat sheet rather than manufacture it as a curved design. If the bone graft material containment structures are provided as pre-shaped structures, they may be pre-curved or pre-shaped so that the structures more accurately fit the anatomy of the site where the stimulation of bone growth is desired. Even though the implants are typically malleable by hand due to their thin nature, structures that are pre-shaped and hold the intended pre-shaped design are included within the scope of this description. This can help reduce operating room time, because the structure is already shaped appropriately.

It should be understood that the parameters of the designs described herein may be configured and/or modified depending upon the use of the implant. Specifically, the thickness of the material, the stiffness of the material, the type of material, and/or the porosity of the material may be adjusted depending upon the particular desired use or application. For example, a smaller defect may call for a structure having a thinner material than a larger defect.

Changes and modifications, additions and deletions may be made to the structures and methods recited above and shown in the drawings without departing from the scope or spirit of the invention.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Sheet Implant for Containment of Bone Graft Material in the Alveolar Ridge

A patient presented desiring a dental implant in the anterior maxilla. A radiograph revealed inadequate bone to support the dental implant. In order to encourage bone growth in the area so that a dental implant may gain purchase into more substantial bone tissue, a surgical site was prepared to receive a bone graft material containment sheet. The bone graft material containment sheet was a 0.25 mm thick sheet of MEDPOR® material (Porex Surgical, Newnan, Ga.) having an average pore size of about 200 microns, and a porosity of about 40%. The sheet was cut to the desired size and tacked to the maxilla. The upper portion of the sheet can also be provided in a T-like shape to provide more surface area for the tacks to be placed. The remainder of the sheet was left long enough so that it wrapped around the bone graft material to be placed inside the shaped sheet. The bone graft material was Medtronic INFUSE® Bone Graft material (which is rhBMP absorbed onto collagen sponge material, Medtronic, Minneapolis, Minn.) mixed with autologous bone chips. Other appropriate bone graft material may be used, including but not limited to those described above, as well as various combinations of such materials. The bone graft material was placed in the defect site. The bone graft material containment sheet was wrapped around the bone graft material and secured to the lingual surface of the maxilla by tucking it between the periosteum and bone. The bone graft material containment sheet was tacked into position again. In some cases, the soft tissue closure over the sheet along with its inherent rigidity may all that is needed to hold the bone graft material containment sheet in place. Next, the gingival tissues were closed over the bone graft material containment sheet with sutures. Examination of the site two weeks after surgery demonstrated good retention of the bone graft material. Examination of the site two months after surgery showed tissue growth into the undersurface of the bone graft material containment sheet.

Portions of the sheet may be removed from the implant, but the remaining sheet is tissue integrated and does not have to be removed, eliminating any harmful stripping of the vascular supply from the regenerated bone. Later, the crestal portion of the sheet was removed, a temporary gingival abutment was inserted, the gingival tissue was closed around the temporary abutment with sutures. Most of the sheet implant remained in place under the gingival tissue, where it was now integrated with the tissue. The sheet implant remained invisible under the tissue and did not disrupt the gingival tissue or detrimentally affect its aesthetic appearance. The fibrovascular tissue that grew through the porous implant supplied blood to the underlying bone graft.

Three months after surgery and after removal of the sutures, healthy gingival tissue was observed around the temporary dental implant abutment. The patient was further evaluated after final restoration of the teeth. The gingiva above the affected dental implant restoration appeared very healthy. The omnidirectional interconnected open pore structure sheet remained under the gingival tissue and was fully integrated with the tissue. In contrast, when titanium mesh is used to contain bone graft material in this way, it typically shows through the gingiva, and it may become exposed, and is often removed by the surgeon in another procedure, interrupting the vascular supply to the underlying bone graft area.

These results demonstrated that the bone graft material containment sheet (MEDPOR) contained the bone graft material in the desired defect site in the maxilla so that new bone was formed. This new bone was used to help stabilize a previously placed prosthesis for insertion of a dental implant.

EXAMPLE 2

Sheet Implant for Containment of Bone Graft Material in a Simultaneous Sinus Lift and Alveolar Ridge Width Graft A patient presented with missing teeth in the posterior maxilla and deficient bone in the area of the missing teeth. The bone was deficient in both height and width in the area where dental implants would be placed. This was called a knife edge ridge because the bone was so thin in this area. The oral surgeon wanted to increase bone width and height in this area. Soft tissues were incised and dissected away from the underlying bone. rhBMP/collagen sponge and synthetic bone graft material called C graft, were used to graft new bone around the knife edge ridge. C graft is a brand name for a synthetic bone graft material made from a marine algae skeleton that has been converted to hydroxyapatite through chemical processing (Algisorb, Osseous Technologies of America, Newport Beach Calif. 92660). C graft was mixed with the collagen sponge and rhBMP to provide extra bulk and a "scaffold" for new bone growth. The oral surgeon cut the sponge of the BMP sponge graft into small pieces and then mixed it with the C graft and used it for the grafted area. Other materials that may be used in this way are autologous bone chips, cadaver bone, xenographic bone particulates or other synthetic bone graft materials, among others. A piece of 0.45 mm thick MEDPOR porous sheet was used to contain the graft mixture and hold it in place. Surgical tacks were placed at the superior edges of the sheet just under the retracted soft tissue.

This graft was placed in conjunction with a sinus lift procedure. An opening was made in the bone above the upper teeth, the open maxillary sinus was entered with dissection of the mucous membrane in the sinus to lift it up and away from the thin bone over the teeth, and then bone graft material was placed in the area to thicken the bone over the missing teeth. The soft tissue was sutured over the graft site and allowed to heal (not shown). The site was inspected and two months later, bone was formed.

Evaluation of the grafted ridge at two months after the insertion of the bone graft containment structure (MEDPOR sheet) containing Medtronic INFUSE® Bone Graft material (which is rhBMP absorbed onto collagen sponge material Medtronic, Minneapolis, Minn.) and synthetic bone graft material called C graft, revealed improved ridge height width and excellent tissue health.

EXAMPLE 3

Sheet Implant for Containment of Bone Graft Material in a Patient with a Congenitally Missing Tooth with an Associated Ridge Deficiency The gingiva was dissected away from the bone. There was a deficiency of bone on the anterior surface and the ridge where the tooth was missing. The oral surgeon planned to place a dental implant into the bone in this area, but the bone was not wide enough to support an implant. A dental implant placed into the bone but since the bone was inadequate to support a loaded implant (one where the tooth is attached), the surgeon wanted to grow new bone over the anterior surface of the implant. Recombinant human BMP (rhBMP) was adsorbed to an acellular collagen sponge used as a bone graft material in the site of missing bone. An omnidirectional interconnected open pore structure sheet of MEDPOR (0.25 mm in thickness) was placed over the bone graft material. The gingiva was then closed with suture over the end of the implant and the graft site.

At two months, healthy tissue was observed over the graft. The underlying porous implant was not visible through the gingival tissue. The end of the dental implant is was exposed at four months, followed by fabrication and placement of the restorative tooth.

EXAMPLE 4

Sheet Implant for Containment of Bone Graft Material in a Patient with a Posterior Maxillary Ridge Width and Height Deficiency A patient presented with missing teeth in the posterior maxilla and deficient bone in the area of the missing teeth. The bone was deficient in both height and width in the area where dental implants would be placed. This was called a knife edge ridge because the bone was so thin in this area. The oral surgeon wanted to increase bone width and height in this area. Soft tissues were incised and dissected away from the underlying bone. rhBMP/collagen sponge and synthetic bone graft material called C graft, were used to graft new bone around the knife edge ridge. C graft was mixed with the collagen sponge and rhBMP to provide extra bulk and a scaffold for new bone growth. The oral surgeon cut the sponge of the BMP sponge graft into small pieces and then mixed it with the C graft and used it for the grafted area. Other materials that may be used in this way are autologous bone chips, cadaver bone, xenographic bone particulates or other synthetic bone graft materials, among others. A piece of 0.45 mm thick MEDPOR porous sheet was used to contain the graft mixture and hold it in place. Surgical tacks were placed at the superior edges of the sheet just under the retracted soft tissue. The soft tissue was sutured over the graft site and allowed to heal (not shown). The site was inspected and two months later, bone was formed.

Evaluation of the grafted ridge at two months after the insertion of the bone graft containment structure (MEDPOR sheet) containing Medtronic INFUSE® Bone Graft material (which is rhBMP absorbed onto collagen sponge material, Medtronic, Minneapolis, Minn.), and synthetic bone graft material called C graft revealed improved ridge height width and excellent tissue health.

EXAMPLE 5

Long Bone Repair

A patient presents in the emergency room with a severe fracture of the tibia following an automobile accident. The tibial bone is deficient in one region. The orthopedic surgeon decides to augment the bone in this deficient region to facilitate healing and strengthening of the bone. In addition to setting the fracture, the surgeon obtains a sheet of the bone containment structure of the present invention, in this case a sheet of MEDPOR. The surgeon grafts the defect with the bone growth material and covers it with a sheet of MEDPOR CONTAIN Mesh which is then screwed or tacked to the bone to prevent displacement of the graft. The bone graft material is located between the bone and the MEDPOR sheet. Radiographs are taken several weeks later and show new bone formation in the tibia where the bone growth material was contained by the MEDPOR sheet.

EXAMPLE 6

Long Bone Repair

A patient presents in the emergency room with a severe fracture of the tibia following an automobile accident. The tibial bone is deficient in one region. The orthopedic surgeon decides to augment the bone in this deficient region to facilitate healing and strengthening of the bone. In addition to setting the fracture, the surgeon obtains a sheet of the bone containment structure of the present invention, in this case a sheet of PEEK. The surgeon obtains a bone growth material and applies it to the sheet of PEEK which is then placed on the bone and secured into place with screws or tacks. The bone graft material is located between the bone and the PEEK sheet. Radiographs are taken several weeks later and show new bone formation in the tibia where the bone growth material was contained by the PEEK sheet.

EXAMPLE 7

Tooth Socket

A patient presents in a dental office requesting insertion of an artificial tooth into the mandible. The dentist examines the socket and obtains radiographs of the site. The dentist concludes that the site has inadequate bone to support the insertion of the artificial tooth. The dentist refers the patient to an oral surgeon who obtains a preformed cylinder with one open end and one closed end of MEDPOR Implant material with wall thickness of approximately 0.3 mm and approximately 40-50% pore volume, and approximately 200 micron pore size.

The oral surgeon fills the socket and the cylinder with bone graft material comprising beta tricalcium phosphate mixed with platelet rich plasma, places the cylinder over the socket and leaves additional sheet material in the form of small flaps in order to attach the flaps to the mandible with tacks or screws. Radiographs taken four weeks later show increased bone density in the tooth socket adjacent to the mandible where the bone graft material is contained by the MEDPOR cylinder. Later, the oral surgeon inserts a dental implant into the newly formed bone. The dental implant is more stable due to the increased bone density.

EXAMPLE 8

Spinal Fusion

A patient with a long history of smoking presents to an orthopedic surgeon with pain radiating down his upper extremities. The surgeon obtains radiographs and observes osteoporosis of several cervical vertebrae and degeneration of the intervertebral discs with resulting compression of cervical spinal nerves. The surgeon recommends spinal fusion of the C5 and C6 cervical vertebrae but is concerned that the osteoporosis may have caused sufficient bone loss to create problems during the spinal fusion and after.

During the surgery and insertion of hardware, the surgeon obtains several strips of MEDPOR sheets and applies them to both lamina of each vertebrae, adhering each strip on three sides with tacks and glue. The strips span the intervertebral space. Next the surgeon inserts a syringe containing a mixture of rhBMP/acellular collagen sponge mixed with hydroxyapatite under the unsecured side of each strip and infuses the mixture into the space between the strip and the lamina of each vertebrae and also between the strip and the intervertebral disc to promote bone growth and improve spinal fusion. The unsecured side is then secured with tacks and glue.

Radiographs taken months later show enhanced bone formation at C5, C6 and in the intervertebral space between C5 and C6. Physical examination reveals decreased vertebral rotation in the C5 and C6 area and reduced pain in the upper extremity.

EXAMPLE 9

Split Calvarial Bone Graft Site Reconstruction

A patient presents with craniofacial trauma resulting in missing bone in the areas of the inferior orbital rim and lateral orbital rim. The surgeon takes a bone graft from the outer table of the patient's calvarium to use in repair of the defect. The donor site, which consists of the inner table of the calvarium without the outer table, is filled with rhBMP/ACS. An interconnected open pore structure material made from laser sintered titanium particles is placed over the outer table defect and the underlying graft material and secured to the outer table with screws. The laser sintered porous material is fabricated in the curvature of the cranium in the area of the defect to closely fit the contour of the cranium. The periosteum and soft tissues are closed over the porous structure. The porous structure prevents the soft tissue from retracting into the defect area which would collapse the rhBMP/ACS graft material.

EXAMPLE 10

Phalanx Crush Injury Repair

A patient presents with a crush injury to a finger in which one phalanx is completely crushed with comminuted bone but the joints are preserved. Using an open approach, the surgeon wraps an omnidirectional interconnected open pore structure plastic sheet with embedded titanium mesh around the comminuted bone fragments, adding bone marrow aspirate from the iliac bone, and secures the ends of the formed cylinder to the edges of the joint area with titanium screws. Soft tissues are closed over the construct and it is splinted during initial healing. Radiographs taken at 1 and 2 months demonstrate increased bone density at the crush site.

EXAMPLE 11

Mandible Augmentation

A patient presents with hemifacial microsomia, with inadequate lateral projection of the right mandibular angle. The surgeon has a prefabricated thin shell of omnidirectional interconnected open pore structure polyethylene material made to the shape of the contralateral mandible outer surface. The surgeon exposes the deficient mandible outer surface, drills multiple holes through the outer table of the mandible surface to access bleeding cancellous bone, fills the porous shell with a mixture of rhBMP/ACS and mineralized freeze dried bone particles, and secures the shell to the outer surface of the deficient mandible with low profile craniofacial screws. Soft tissues are closed over the site to allow healing. Radiographs taken at 1 and 2 months demonstrate increased bone density at the right mandibular angle.

EXAMPLE 12

A Full Thickness Calvarial Defect Repair

A patient presents with a full thickness calvarial defect in the temporal-parietal area due to benign cyst excision. The surgeon exposes the defect and covers the dura with a thin omnidirectional interconnected open pore structure sheet of polypropylene with a barrier surface adjacent to the dura. Bone graft material, consisting of cancellous bone from the iliac crest mixed with rhBMP/ACS is placed to fill the defect, and covered with a thin omnidirectional interconnected open pore structure sheet of polypropylene, which has been reinforced with embedded titanium mesh. The outer sheet is fixed to the outer table of the calvarium with craniofacial screws. The overlying tissues are closed. Radiographs taken at 2 and 3 months demonstrate increased bone density at the site of the calvarial defect.

EXAMPLE 13

Repair of a Mandibular Continuity Defect

A continuity defect of the mandible is created due to excision of osseonecrotic tissue of the mandible. The defect is from the mandible angle to the mentum. Using a computed tomographic X ray scan of the patient, the proper shape of the missing mandible segment is created in a computer. Computer numeric controlled (CNC) machining is used to create a metal reproduction of the mandible with the proper shape of the missing mandible segment. Polypropylene mesh is tightly wrapped around the mandible shape in multiple layers to create an omnidirectional interconnected pore structure due to the multiple layers mesh built up on the metal mandible form, overlapping the edges of the defect area. The entire construct is placed in an oven and heated to sintering temperature to fuse the layers of the mesh together without disrupting the porous structure. The metal form is cut near one edge of the defect, and the omnidirectional interconnected open pore structure is slipped off the metal mold. The structure is packaged and sterilized with ethylene oxide. In surgery, the structure is filled with a mixture of rhBMP/acellular collagen sponge, cancellous bone from the patient's iliac bone, and marine algae-derived particulate hydroxyapatite particles. The construct with the bone graft material is inserted into place, and the edges are trimmed as needed and slipped over the ends of the remaining mandible segments. A titanium mandible reconstruction plate is placed over the entire construct to achieve rigid fixation during healing. The plate is removed approximately 6 months later after the new bone has formed.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A method of facilitating growth of bone at a desired location comprising:
shaping, by bending, a biocompatible, non-resorbable porous material comprising a porous matrix of interconnected pores into a shaped porous material for placement into the desired location, the shaped porous material comprising a base portion, a side portion, and a top portion, the side portion sharing a first shaped edge with the base portion to define an interior region of the shaped porous material, the top portion being hingedly attached to a second shaped edge of the side portion such that the top portion forms open and closed positions with the side portion, the top portion providing an opening into the interior region in the open position;
placing a bone graft material inside the interior region of the shaped porous material;
placing the top portion in the closed position by bending the top portion relative to the side portion at the second shaped edge to cover the placed bone graft material;
stably fixing the shaped porous material containing the bone graft material to structures adjacent to the desired location; and
permitting bone to grow in the desired location.

2. The method of claim 1, wherein after fixing the shaped porous material containing the bone graft material to structures adjacent to the desired location, soft tissues are closed over the shaped porous material.

3. The method of claim 1, further comprising permitting blood vessels to infiltrate into the shaped porous material.

4. The method of claim 1, wherein the porous material is formed by sintering particles of polymer or metal into the desired shape.

5. The method of claim 1, wherein the porous material further comprises a metal mesh, a metal wire, or multiple layers of metal mesh or metal wire sintered together.

6. The method of claim 1, wherein the bone graft material is bone, a synthetic material, a growth factor, a cell, or a combination thereof.

7. The method of claim 6, wherein the bone is autologous bone, autologous bone particulate, allogenic bone, human cadaver bone, xenograft bone, animal bone, or bone chips.

8. The method of claim 6, wherein the synthetic material is hydroxyapatite, calcium phosphate, ceramics, bioactive glass, calcium sulfate, or a polymer-based bone graft substitute.

9. The method of claim 6, wherein the growth factor is bone morphogenic protein (BMP), a BMP mimetic, recombinant human bone morphogenic protein 2 (rhBMP-2), platelet-rich plasma (PRP), transforming growth factor-beta (TGF-beta), platelet-derived growth factor (PDGF), recombinant human platelet derived growth factor (rhPDGF), insulin-like growth factor, fibroblast growth factor, a xenographic bone protein, a growth differentiation factor, calcitonin, or a calcitonin mimetic.

10. The method of claim 6, wherein the cell is a stem cell, a bone marrow cell, a mesenchymal stem cell, or a combination thereof.

11. The method of claim 1, wherein the porous matrix contains pores of average diameter of 40 to about 1000 microns, about 100 to about 800 microns, about 100 to about 500 microns, about 50 to about 500 microns, about 60 to about 400 microns, about 200 to about 400 microns, or about 100 to about 200 microns.

12. The method of claim 1, wherein the porous material has a pore volume from about 20% to about 60%, or from about 40% to about 50%.

13. The method of claim 1, wherein the porous material has a thickness of about 0.1 to about 2.0 mm, about 0.1 to about 1.0 mm, about 0.1 to about 0.9 mm, about 0.1 to about 0.8 mm, about 0.2 to about 0.4 mm, about 0.2 to about 0.3 mm, or about 0.25 mm.

14. The method of claim 1, wherein the pores are omni-directional.

15. The method of claim 1, wherein the pores are multi-dimensional.

16. The method of claim 1, wherein the porous material is sintered polyethylene, the pores are in the range of about 40 to about 1000 microns in average diameter, the pore volume is about 20% to about 60%, and the porous material is about 0.1 to about 3.0 mm in thickness.

17. The method of claim 1, wherein the shaped porous material includes opposing side portions, and wherein the shaped porous material is placed in a trough-like manner between the bone graft material and the desired location to contain the bone graft material.

18. The method of claim 1, further comprising inserting a bone plate through the porous material and the structures adjacent to the desired location, the structures being bone.

19. The method of claim 18, wherein the bone plate includes openings therethrough.

20. The method of claim 1, wherein the shaped porous material has a cylindrical-like shape.

21. The method of claim 1, wherein the shaped porous material is box-shaped.

* * * * *